United States Patent
Dann et al.

(10) Patent No.: US 6,921,828 B2
(45) Date of Patent: Jul. 26, 2005

(54) PROCESSES FOR THE PREPARATION OF 2-AMINOMETHLPYRIDINES AND THE 2-CYANOPYRIDINES USED IN THEIR PREPARATION

(75) Inventors: Norman Dann, Cambridgeshire (GB); Peter Dominic Riordan, Bristol (GB); Mehul Rasikchandra Amin, Suffolk (GB); Michael Mellor, Suffolk (GB)

(73) Assignee: Bayer CropScience S.A. (FR)

( * ) Notice: Subject to any disclaimer, the term of this patent is extended or adjusted under 35 U.S.C. 154(b) by 51 days.

(21) Appl. No.: 10/362,728
(22) PCT Filed: Aug. 21, 2001
(86) PCT No.: PCT/EP01/10984
§ 371 (c)(1),
(2), (4) Date: Jun. 11, 2003
(87) PCT Pub. No.: WO02/16322
PCT Pub. Date: Feb. 28, 2002

(65) Prior Publication Data
US 2004/0049048 A1 Mar. 11, 2004

(30) Foreign Application Priority Data

| Aug. 25, 2000 | (GB) | ............................................. 0021066 |
| Oct. 19, 2000 | (GB) | ............................................. 0025616 |
| Jun. 7, 2001 | (EP) | ............................................. 01420128 |

(51) Int. Cl.[7] ............................................. C07D 211/78
(52) U.S. Cl. ........................ 546/286; 546/329; 546/337; 546/345
(58) Field of Search .................. 546/286, 339, 546/337, 345

(56) References Cited

U.S. PATENT DOCUMENTS

| 4,159,382 A | | 6/1979 | Garrou | |
| 4,766,219 A | * | 8/1988 | Orvik et al. | ................. 546/286 |
| 4,851,539 A | * | 7/1989 | Johnston et al. | ............ 546/345 |
| 5,300,650 A | * | 4/1994 | Nabata | ........................ 546/329 |
| 5,424,437 A | | 6/1995 | Ieno et al. | ................... 546/329 |
| 5,453,506 A | | 9/1995 | Diehr | ......................... 546/329 |
| 5,478,944 A | | 12/1995 | Kraus | ......................... 546/250 |

FOREIGN PATENT DOCUMENTS

| EP | 0034917 | 9/1981 |
| EP | 0369208 | 5/1990 |
| EP | 0535518 | 4/1993 |
| JP | 61-251663 | 11/1986 |
| JP | 04243867 | 11/1993 |
| JP | 7138209 | 8/1995 |
| JP | 8053417 | 5/1996 |
| JP | 9176121 | 9/1997 |
| JP | 10231288 | 11/1998 |
| JP | 10330362 | 3/1999 |
| JP | 2000256283 | 12/2000 |
| WO | 92/18487 | 10/1992 |
| WO | 99/42447 | 8/1999 |
| WO | 0117970 | 3/2001 |
| WO | WO 01/17970 | 3/2001 |

* cited by examiner

*Primary Examiner*—Cecilia J. Tsang
*Assistant Examiner*—Raymond Covington
(74) *Attorney, Agent, or Firm*—Ostrolenk, Faber, Gerb & Soffen, LLP

(57) ABSTRACT

The invention relates to a process for the preparation of a compound of formula (V), according to the following scheme: wherein the various substituents are as defined in the description

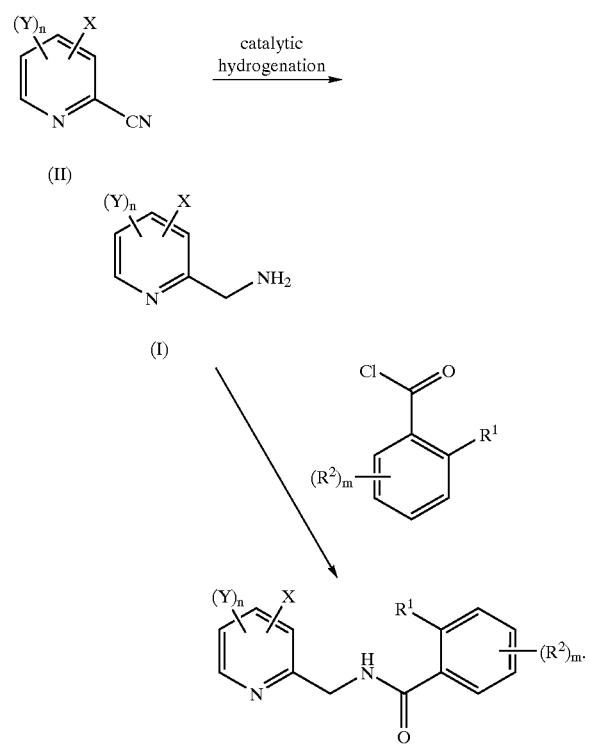

21 Claims, No Drawings

PROCESSES FOR THE PREPARATION OF 2-AMINOMETHLPYRIDINES AND THE 2-CYANOPYRIDINES USED IN THEIR PREPARATION

This invention relates to novel processes for the preparation of 2-aminomethylpyridines (particularly 2-aminomethyl-3-chloro-5-trifluoromethylpyridine), and for the preparation of 2-cyanopyridines used in their preparation, which compounds are useful as intermediates for the production of pesticides.

The catalytic reduction of cyanopyridines to give aminomethylpyridines is known. However when the cyanopyridine compounds contain additional halogen atom(s) the reduction may be complicated by the competing dehalogenation reaction. It is stated by P. N. Rylander, *Hydrogenation Methods* (Best Synthetic Series, published by Academic Press), (1985), page 148, that palladium is usually the catalyst of choice when wishing to effect a dehalogenation reaction, and that platinum and rhodium are relatively ineffective and are hence often used in hydrogenations where the halogen is to be preserved.

In contrast with the above prior art teaching we have found that the use of a palladium catalyst gives particularly good results in the reduction of cyanopyridines which contain additional halogen atom(s). We have developed a new process for the preparation of 2-aminomethylpyridines, which contain additional halogen atom(s) in which minimal dehalogenation occurs, and which is applicable to industrial scale processes.

There have been a number of procedures published for introducing a cyano group at the 2-position of a pyridine moiety. These typically involve substitution of a halogen, in particular bromine or fluorine, in a polar solvent, e.g. dimethyl sulphoxide or dimethylformamide. In addition, there are numerous methods starting from the activated pyridine N-oxide or N-alkylpyridine. Many of these cyanation routes use heavy metal reagents, containing copper or nickel. For example, EP0034917 discloses the preparation of 2-cyano-3-chloro-5-trifluoromethylpyridine from the 2-bromo analogue by reaction with cuprous cyanide in dimethylformamide at 120° C.

However, many of these prior art processes suffer from one or more drawbacks, including poor yields, use of heavy metals which produce toxic effluents, or polar solvents which are difficult to recover. Further, methods which involve formation of the pyridine N-oxide or N-alkylpyridine involve several steps. These drawbacks are more critical on scale-up to industrial scale.

International patent application WO 01-17970 describes the cyanation of 2-halopyridine compounds with an activating agent and a cyanide source in a polar solvent and thus avoids many of the above disadvantages. However there still remains with this procedure the need to recycle the activating agent and the aprotic solvent in order to minimise the costs for an industrial scale process.

We have now developed an alternative and improved process for the preparation of 2-cyanopyridines which is applicable to industrial scale processes.

According to a first aspect of the present invention, there is provided a process (A) for the preparation of a compound of general formula (I):

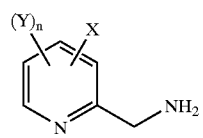

or a salt thereof, which process comprises the catalytic hydrogenation of a compound of general formula (II):

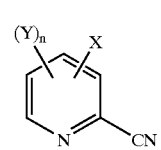

or a salt thereof,
wherein X is halogen; each Y, which may be the same or different, is halogen, haloalkyl, alkoxycarbonyl or alkylsulphonyl; and n is 0 to 3.

In this invention halogen means a fluorine, chlorine or bromine atom. The preferred halogen atom is chlorine.

Haloalkyl typically means a $C_1$ to $C_6$ alkyl moiety substituted by one or more halogen atoms. For example the $C_1$ to $C_6$ alkyl moiety may be methyl, ethyl, n-propyl or i-propyl, preferably methyl. The $C_1$ to $C_6$ alkyl moiety is preferably substituted by one or more chlorine or fluorine atoms. A more preferred haloalkyl group is trifluoromethyl.

An alkoxycarbonyl group is typically $C_1$ to $C_6$ alkoxycarbonyl such as methoxycarbonyl, ethoxycarbonyl, n-propoxycarbonyl or i-propoxycarbonyl.

An alkylsulphonyl group is typically $C_1$ to $C_6$ alkylsulphonyl in which the $C_1$ to $C_6$ moiety is as defined above.

Preferably X is chlorine.

Preferably Y is halogen or haloalkyl (more preferably trifluoromethyl).

Compound (II) is preferably 3-chloro-2-cyano-5-trifluoromethylpyridine.

The catalyst generally comprises a metal selected from palladium, platinum, ruthenium, nickel and cobalt. The amount of metal in the catalyst used (which is generally supported on for example charcoal) is generally from 0.05–0.7% by weight relative to the amount of the compound of formula (II), preferably from 0.05–0.3%, more preferably from 0.1–0.2%. A preferred catalyst contains palladium, for example finely divided palladium on an inert carrier such as charcoal. This has been found to give both a convenient reaction rate and minimal side reactions. Thus when the compound of formula (II) is 3-chloro-2-cyano-5-trifluoromethylpyridine, minimal dechlorination occurs when using the process of the invention. Other examples of suitable catalysts include catalysts comprising oxides or other compounds of the above mentioned metals.

The process is typically carried out in the presence of a solvent such as an alcohol, for example methanol, ethanol, propanol or butanol, or an ester such as ethyl acetate, or an ether such as tetrahydrofuran. Alcohol solvents are preferred (methanol is most preferred). The process is preferably performed in the presence of a strong acid such as hydrochloric acid, hydrobromic acid, sulphuric acid or phosphoric acid (preferably hydrochloric acid). The presence of the acid helps prevent poisoning of the catalyst by the amino group of the product of formula (I), and also prevents the coupling of amino intermediates which is otherwise known to occur during the catalytic hydrogenation of nitriles.

The reaction conditions typically comprise combining all reactants in a suitable reaction vessel and stirring, for example at a temperature of from 0 to 60° C., preferably from 20 to 30° C. A further advantage of the process is that low pressures are used, with a hydrogen pressure of from 1 to 4 atmospheres generally being employed (the process is preferably performed at 1 atmosphere).

The reaction is optionally performed in the presence of a catalyst inhibitor, which can lead to a further improvement in the reaction selectivity by reducing the amount of dehalogenation which may occur as a side reaction. Such catalyst inhibitors are known in the art, for example as described in P. N. Rylander in Hydrogenation Methods (Best Synthetic Series, published by Academic Press), 1985, pages 125–126, and include alkali metal bromides or iodides such as potassium bromide and potassium iodide; or ammonium bromide or ammonium iodide; or hydrogen bromide or hydrogen iodide; or phosphorus compounds such as triphenyl phosphite, hypophosphorous acid, phosphorous acid or alkylphosphinic acids; or thiodiglycol (2,2'-thiodiethanol); or thiourea; or sulphur. Preferably the catalyst inhibitor is selected from an alkali metal bromide or iodide, ammonium bromide or iodide and hydrogen iodide.

The present invention thus provides a high yielding, selective and convenient process for the preparation of 2-aminomethylpyridines.

It is particularly convenient to generate the compound of formula (I) in the form of a salt, especially a hydrochloride salt. When used as an intermediate in the production of a pesticide the salt can be submitted directly to the next reaction step without prior isolation of the corresponding free amine. The production of the salt and its subsequent reaction can therefore be conveniently carried out in a single vessel. A particularly preferred salt is 2-aminomethyl-3-chloro-5-trifluoromethylpyridine hydrochloride.

According to a further feature of the present invention, there is provided a process (B) for the preparation of a compound of general formula (II) as defined above which comprises treating a compound of general formula (III):

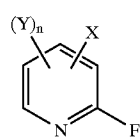

(III)

with a cyanide source and a catalyst in an aqueous solvent or without solvent,
wherein X, Y and n are as hereinbefore defined; and wherein the cyanide source is hydrogen cyanide, an alkali metal cyanide, an alkaline earth metal cyanide or an optionally substituted ammonium cyanide.

The catalyst is generally a phase transfer catalyst such as a tetraalkyl ammonium salt such as benzyl trimethylammonium chloride, tricaprylylmethylammonium chloride, tetramethylammonium chloride, tetra-n-propylammonium bromide, n-dodecyl trimethylammonium chloride, tetra-n-butylammonium chloride, tetra-n-butylammonium bromide, tetra-n-octylammonium bromide or n-tetradecyl trimethylammonium bromide; or a tetraalkyl phosphonium salt such as tetra-n-butylphosphoniun bromide or tetraphenylphosphonium bromide; or a crown ether or acyclic analogue thereof such as TDA-1 (tris[2-(2-methoxyethoxy)ethyl] amine); or an amine such as 4-dimethylaminopyridine.

Preferably the catalyst is selected from tricaprylylmethylammonium chloride and tetra-n-octylammonium bromide.

The amount of catalyst used is generally from about 0.01 to 10 mol %, preferably from about 0.1 to 5 mol %, more preferably from about 1 to 5 mol %.

Compound (III) is preferably 3-chloro-2-fluoro-5-trifluoromethylpyridine.

The above process (B) of the invention is a high yielding process for the preparation of 2-cyanopyridines, which is simple to perform and operates at moderate temperatures and does not suffer from the drawbacks of many prior art processes. In particular the process of the invention does not require heavy metal cyanides such as copper or nickel cyanide, which, when used on an industrial scale, produce toxic effluent streams and are difficult to recover. The process (B) of the invention produces waste streams, which are readily treatable.

In addition, the process does not require the preparation of activated pyridine N-oxide or N-alkylpyridine for high conversions, which is a requisite for many of the prior art processes. The process (B) of the invention does not require an activating agent such as 4-dimethylaminopyridine and hence avoids additional recovery and recycling steps. A further advantage of the process (B) of the invention is that organic solvents are not used in the reaction, thus avoiding the need to recycle expensive solvents such as dimethyl sulphoxide.

The cyanide source is preferably sodium cyanide or potassium cyanide, preferably potassium cyanide. The amount of cyanide source used is generally from about 1.0 to about 2.0 molar equivalents (however more may be used if desired), preferably from 1.0 to 1.5 molar equivalents, more preferably from 1.0 to 1.1 molar equivalents.

The reaction is generally and preferably performed using water as solvent, however it may also be carried out in the absence of solvent.

The reaction conditions typically comprise combining all reactants in a suitable reaction vessel and stirring at a temperature of from 10 to 60° C., preferably from 20 to 40° C.

The present invention thus provides a high yielding process (B) for the preparation of 2-cyanopyridines. Since the reaction uses moderate reaction temperatures, simple and inexpensive reactors and downstream processing equipment is all that is required. Furthermore, since the reactants are readily available, the process is inexpensive to operate. In addition, the present process produces waste streams that are readily treatable.

According to a further feature of the invention the processes (B) and (A) can be combined to prepare a compound of formula (I) from a compound of formula (III).

According to a further feature of the invention the process (A), or the combined processes (B) and (A), is followed by a further process step (C) which comprises the acylation of said compound (I) with a benzoyl compound of formula (IV):

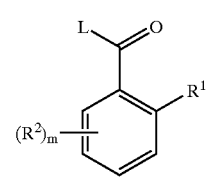

(IV)

wherein L is a leaving group; $R^1$ and $R^2$ each represent the same or different halogen; and m is 0, 1 or 2, to give a compound of formula (V):

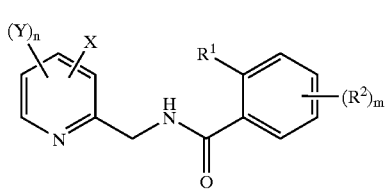

(V)

Preferably L is chlorine.

Compounds of Formula (V) are valuable pesticide active ingredients disclosed for example in International Patent Publication Number WO 99/42447.

Preferred compounds of formula (V) are:

N-[(3-chloro-5-trifluoromethyl-2-pyridyl)methyl]-2,6-dichlorobenzamide;

N-[(3-chloro-5-trifluoromethyl-2-pyridyl)methyl]-2,6-difluorobenzamide;

N-[(3-chloro-5-trifluoromethyl-2-pyridyl)methyl]-2-chloro-6-fluorobenzamide;

N-[(3-chloro-5-trifluoromethyl-2-pyridyl)methyl]-2,3-difluorobenzamide;

N-[(3-chloro-5-trifluoromethyl-2-pyridyl)methyl]-2,4,6-trifluorobenzamide or

N-[(3-chloro-5-trifluoromethyl-2-pyridyl)methyl]-2-bromo-6-chlorobenzamide.

Process step (C) is described in International Patent Publication Number WO 99/42447.

According to a further feature of the invention the process (B), or the combined processes (B) and (A), or (B), (A) and (C) can be combined with an earlier process step (D) which comprises the fluorination of a compound of formula (VI):

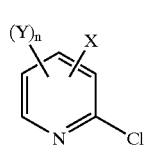

(VI)

wherein X, Y and n are as defined above.

The process step (D) is generally performed using a suitable fluorinating agent such as an alkali metal fluoride, preferably potassium fluoride or sodium fluoride, in an aprotic solvent such as dimethyl sulphoxide or sulpholane, at a temperature of from 50° C. to 150° C.

The compounds of formula (I) and (II) obtained by the above processes of the invention are particularly useful in the preparation of fungicidally active 2-pyridylmethylamine derivatives of formula (V), according to the following reaction scheme:

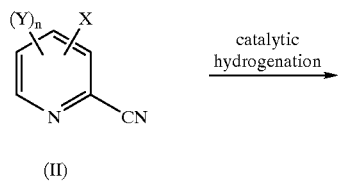

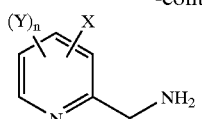

(I)

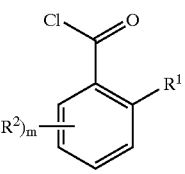

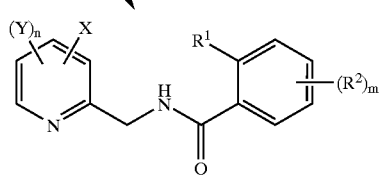

(V)

The present invention is further illustrated by the following preparative examples:

EXAMPLE 1 (PROCESS STEP A)

A mixture of 3-chloro-2-cyano-5-trifluoromethylpyridine (5.1 g) and 5% palladium on charcoal (5.1 mg as Pd metal) was stirred at 20° C. with methanol and concentrated hydrochloric acid (2.5 ml) under 1 atmosphere of hydrogen. After 4 hours the reaction was judged to be complete by hplc. The mixture was filtered through Celatom, washed with methanol and water and evaporated to give 2-aminomethyl-3-chloro-5-trifluoromethylpyridine hydrochloride in 95–97% yield, NMR (in $D_2O$) 4.6 (s, 2H), 8.35 (s, 1H), 8.9 (s, 1H).

EXAMPLE 2 (PROCESS STEP B)

A solution of potassium cyanide (71.6 g) in water (215 g) was added during 1 hour to a stirred mixture of 3-chloro-2-fluoro-5-trifluoromethylpyridine (199.5 g) and Aliquat 336 (tricaprylylmethylammonium chloride, 12.1 g) at 30° C. Stirring was maintained at this temperature for 4 hours at which time the amount of starting fluoride was less than 1% by hplc. The lower organic phase was separated and washed with aqueous sodium chloride solution and distilled to give 3-chloro-2-cyano-5-trifluoromethylpyridine (185.8 g, 90% yield) bp 90° C. at 15 mbar. The purity of this product was 98%.

EXAMPLE 3 (PROCESS STEP B)

Solid sodium cyanide (0.29 g) was added to a stirred mixture of 3-chloro-2-fluoro-5-trifluoromethylpyridine (0.8 g) and tetrabutylammonium bromide (0.06 g) at 20–25° C., and stirred for 23 hours to give 3-chloro-2-cyano-5-trifluoromethylpyridine (0.68 g, 82% yield by hplc).

EXAMPLE OF PROCESS STEP (D)

2,3-Dichloro-5-trifluoromethylpyridine (800 g) was added to a stirred mixture of anhydrous potassium fluoride (320 g) and anhydrous dimethylsulphoxide at 110° C. then heated at 120° C. for 2 hours and fractionally distilled under reduced pressure to give 3-chloro-2-fluoro-5-trifluoromethylpyridine (685 g) in a yield of 92% (98% purity).

What is claimed is:

1. A process for the preparation of a compound of general formula (I):

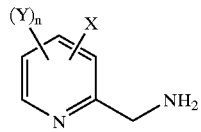

or a salt thereof, which process comprises the catalytic hydrogenation of a compound of general formula (II):

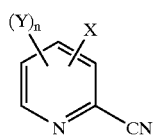

or a salt thereof, wherein X is halogen; each Y, which may be the same or different, is halogen, haloalkyl, alkoxycarbonyl or alkylsulphonyl; and n is 0 to 3, in the presence of a catalyst comprising palladium; in a solvent and at a temperature in the range of from 0° C. to 60° C.

2. A process according to claim 1 in which X is chlorine.

3. A process according to claim 1 in which Y is halogen or haloalkyl.

4. A process according to claim 3 in which Y is trifluoromethyl.

5. A process according to claim 1 in which the amount of metal in the catalyst is from 0.05 to 0.7% by weight relative to the amount of the compound of formula (II).

6. A process according to claim 1 in which the amount of metal in the catalyst is from 0.05 to 0.3% by weight relative to the amount of the compound of formula (II).

7. A process according to claim 1 in which the amount of metal in the catalyst is from 0.1 to 0.2% by weight relative to the amount of the compound of formula (II).

8. A process according to claim 1 which is conducted in the presence of an alcohol solvent.

9. A process according to claim 8 wherein the alcohol solvent is methanol.

10. A process according to claim 1 which is performed at a hydrogen pressure of from 1 to 4 atmospheres.

11. A process according to claim 1 which is performed in the presence of a catalyst inhibitor.

12. A process according to claim 11 in which the catalyst inhibitor is selected from the group consisting of alkali metal bromides, alkali metal iodides, ammonium bromide, ammonium iodide, hydrogen bromide, and hydrogen iodide.

13. A process according to claim 1 in which the compound of formula (II) is 3-chloro-2-cyano-5-trifluoromethylpyridine.

14. The process of claim 1 further comprising the step of acylating compound (I) with a benzoyl compound of formula (IV):

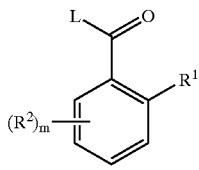

wherein L is a leaving group; $R^1$ and $R^2$ each represent the same or different halogen; and m is 0, 1 or 2, to produce a compound of formula (V):

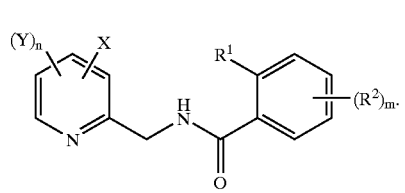

15. A process according to claim 1 which is performed in the presence of a strong acid selected from the group consisting of hydrochloric acid, hydrobromic acid, sulphuric acid, and phosphoric acid.

16. The process of claim 15 wherein the strong acid is hydrochloric acid.

17. The process of claim 14 wherein the compound of formula (V) is selected from the group consisting of:
   N-[(3-chloro-5-trifluoromethyl-2-pyridyl)methyl]-2,6-dichlorobenzamide,
   N-[(3-chloro-5-trifluoromethyl-2-pyridyl)methyl]-2,6-difluorobenzamide,
   N-[(3-chloro-5-trifluoromethyl-2-pyridyl)methyl]-2-chloro-6-fluorobenzamide,
   N-[(3-chloro-5-trifluoromethyl-2-pyridyl)methyl]-2,3-difluorobenzamide,
   N-[(3-chloro-5-trifluoromethyl-2-pyridyl)methyl]2,4,6-trifluorobenzamide, and
   N-[(3-chloro-5-trifluoromethyl-2-pyridyl)methyl]-2-bromo-6-chlorobenzamide.

18. A process for the preparation of a compound of the formula (I):

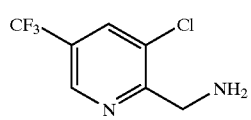

or a salt thereof, which process comprises the catalytic hydrogenation of a compound of the formula (II):

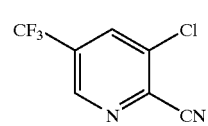

or a salt thereof, in the presence of:
   (A) a strong acid selected from the group consisting of hydrochloric acid, hydrobromic acid, sulphuric acid, and phosphoric acid,
   (B) a catalyst comprising palladium, (C) a catalyst inhibitor selected from the group consisting of alkali metal bromides, alkali metal iodides, ammonium bromide, ammonium iodide, hydrogen bromide, and hydrogen iodide;

in methanol and at a temperature in the range of from 0° C. to 60° C.

19. The process of claim 18 wherein the strong acid is hydrochloric acid.

20. The process of claim 18 further comprising the step of acylating compound (I) with a beazoyl compound of formula (IV):

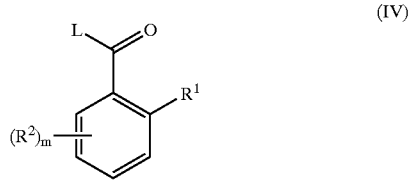

(IV)

wherein L is a leaving group; $R^1$ and $R^2$ each represent the same or different halogen; and m is 0, 1 or 2, to produce a compound of formula (V):

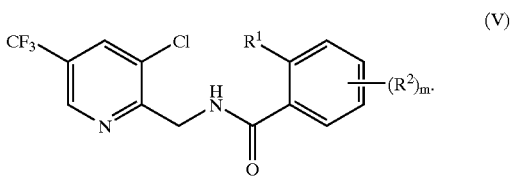

(V)

21. The process of claim 19 wherein the compound of formula (V) is selected from the group consisting of:
 N-[(3-chloro-5-trifluoromethyl-2-pyridyl)methyl]-2,6-dichlorobenzamide,
 N-[(3-chloro-5-trifluoromethyl-2-pyridyl)methyl]-2,6-difluorobenzamide,
 N-[(3-chloro-5-trifluoromethyl-2-pyridyl)methyl]-2-chloro-6-fluorobenzamide,
 N-[(3-chloro-5-trifluoromethyl-2-pyridyl)methyl]-2,3-difluorobenzamide,
 N-[(3-chloro-5-trifluoromethyl-2-pyridyl)methyl]2,4,6-trifluorobenzamide, and
 N-[(3-chloro-5-trifluoromethyl-2-pyridyl)methyl]-2-bromo-6-chlorobenzamide.

* * * * *